US012691255B2

(12) United States Patent
Hilas et al.

(10) Patent No.: US 12,691,255 B2
(45) Date of Patent: Jul. 28, 2026

(54) MEDICAL INTRODUCER AND SHEATH

(71) Applicant: Cook Medical Technologies LLC, Bloomington, IN (US)

(72) Inventors: Georgios T. Hilas, Bloomington, IN (US); Quentin T. Hillen, Elletsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 477 days.

(21) Appl. No.: 18/225,810

(22) Filed: Jul. 25, 2023

(65) Prior Publication Data

US 2024/0058582 A1 Feb. 22, 2024

Related U.S. Application Data

(60) Provisional application No. 63/399,299, filed on Aug. 19, 2022.

(51) Int. Cl.
*A61M 25/01* (2006.01)

(52) U.S. Cl.
CPC .............................. *A61M 25/0108* (2013.01)

(58) Field of Classification Search
CPC .......... A61M 25/0108; A61M 25/0068; A61M 25/0045; A61M 25/005; A61M 25/001; A61M 25/0012; A61M 2025/0681; A61M 2025/0034
See application file for complete search history.

(56) References Cited

U.S. PATENT DOCUMENTS

| | | | |
|---|---|---|---|
| 5,380,304 A | 1/1995 | Parker | |
| 5,700,253 A | 12/1997 | Parker | |
| 6,416,499 B2 | 7/2002 | Paul, Jr. | |
| 7,985,213 B2 | 7/2011 | Parker | |
| 8,152,767 B2 | 4/2012 | Valaie | |
| 8,206,373 B2 | 6/2012 | Zhou | |
| 8,235,968 B2 * | 8/2012 | Tremaglio | ........ A61M 25/0054 |
| | | | 604/525 |

(Continued)

FOREIGN PATENT DOCUMENTS

| | | | |
|---|---|---|---|
| EP | 1062965 | 12/2000 | |
| EP | 1062965 B1 * | 9/2004 | ............. A61L 29/18 |

(Continued)

OTHER PUBLICATIONS

European Patent Office, Extended European Search Report, Application No. 23192267.5, Feb. 8, 2024, 11 pages, European Patent Office, Munich, Germany (Year: 2024).*

*Primary Examiner* — Andrew M Gilbert
(74) *Attorney, Agent, or Firm* — Liell & McNeil

(57) ABSTRACT

A medical introducer includes a dilator received in an introducer sheath that includes a composite tube extending between a valve and a tip. The composite tube includes a braid with a hollow cylindrical shape sandwiched between an inner polymer tube and outer thermoplastic tube. The tip includes a loaded thermoplastic radiopaque marker, and a crosslinked polymer sleeve with an outer surface that has a flush transition to an outer surface of the composite tube. The radiopaque marker includes a tapered segment, and the crosslinked polymer sleeve extends distally beyond the polymer tube and serves to reinforce, protect and shape the distal introducer sheath tip.

20 Claims, 6 Drawing Sheets

(56) References Cited

U.S. PATENT DOCUMENTS

| | | | | |
|---|---|---|---|---|
| 8,444,802 | B2 | 5/2013 | Lee et al. | |
| 8,628,496 | B2 | 1/2014 | Valaie | |
| 8,671,817 | B1 | 3/2014 | Bogusky | |
| 8,702,679 | B2* | 4/2014 | Deckman | A61M 25/005 |
| | | | | 604/523 |
| 8,708,997 | B2 | 4/2014 | Parker | |
| 8,734,699 | B2 | 5/2014 | Heideman et al. | |
| 9,149,600 | B2* | 10/2015 | Stigall | B29C 65/68 |
| 9,399,114 | B2 | 7/2016 | Parker | |
| 9,757,541 | B2* | 9/2017 | Haarer | A61M 25/0662 |
| 9,895,511 | B2 | 2/2018 | Rasmussen | |
| 10,046,138 | B2* | 8/2018 | Faherty | A61M 25/0045 |
| 10,398,874 | B2 | 9/2019 | Williams et al. | |
| 10,631,985 | B2 | 4/2020 | Gallagher | |
| 10,864,357 | B2 | 12/2020 | Kume et al. | |
| 11,000,670 | B2* | 5/2021 | Connors, III | A61M 25/0054 |
| 11,191,566 | B2* | 12/2021 | Cise | A61M 39/0247 |
| 11,285,294 | B2 | 3/2022 | McElhaney et al. | |
| 11,623,067 | B2* | 4/2023 | Jackson | B29C 53/00 |
| | | | | 604/525 |

| | | | | |
|---|---|---|---|---|
| 2002/0156459 | A1* | 10/2002 | Ye | A61L 29/085 |
| | | | | 604/527 |
| 2006/0095050 | A1* | 5/2006 | Hartley | A61M 25/0662 |
| | | | | 606/108 |
| 2008/0108974 | A1* | 5/2008 | Yee Roth | A61L 29/085 |
| | | | | 604/529 |
| 2012/0310212 | A1* | 12/2012 | Fischell | A61M 25/0054 |
| | | | | 604/523 |
| 2019/0344051 | A1* | 11/2019 | Ouchi | A61M 25/0138 |
| 2019/0366036 | A1* | 12/2019 | Jalgaonkar | A61M 25/008 |
| 2020/0276413 | A1* | 9/2020 | Katsurada | A61B 17/3207 |
| 2023/0172658 | A1* | 6/2023 | Luk | A61B 18/1492 |
| | | | | 606/41 |
| 2023/0240694 | A1* | 8/2023 | Panian | A61M 25/0082 |
| 2025/0249205 | A1* | 8/2025 | Ito | A61M 25/0023 |

FOREIGN PATENT DOCUMENTS

| | | | | |
|---|---|---|---|---|
| EP | 3056238 A1 * | 8/2016 | | A61M 25/0012 |
| WO | WO03020353 | 3/2003 | | |
| WO | 2011123222 | 10/2011 | | |

* cited by examiner

MEDICAL INTRODUCER AND SHEATH

TECHNICAL FIELD

The present disclosure relates generally to medical introducers, and more particularly to introducer sheath tip structures.

BACKGROUND

Physicians know that advancing introducers through tight and/or scared tissue can be challenging due to the exposure of the sheath distal tip to engagement with surrounding tissue. The introducer sheath includes a distal taper contour from an outer diameter of the introducer sheath down to the outer diameter of the supporting dilator. Variations in tip geometry and any gap between the tip and the dilator can lead to undesirable so called "toe nailing", where the tip digs into tissue at a tip edge or gap. Other less-than-tight interface to the supporting dilator can also be problematic. Apart from this issue, there remains room for improving the positioning of radiopaque markers relative to the distal tip end of introducer sheaths to improve precise positioning in a patient's anatomy. Also, radiopaque markers for introducer sheaths, especially when presented in the form of a loaded thermoplastic, can be at risk for oxidation, and maybe even induced embrittlement.

The present disclosure is directed to one or more of the problems set forth above.

SUMMARY

An introducer sheath includes a composite tube that extends between a valve and a tip, and includes a braid with a hollow cylindrical shape sandwiched between an inner polymer tube and an outer thermoplastic tube. The tip includes a loaded thermoplastic radiopaque marker at least partially covered by a crosslinked polymer sleeve that receives a distal segment of the composite tube. An outer surface of the proximal end of the crosslinked polymer sleeve has a flush transition to an outer surface of the composite tube, and a distal portion of the crosslinked polymer sleeve extends distally beyond a distal end of the inner polymer tube. The radiopaque marker has a tapered segment distal to the flush transition.

In another aspect, an introducer includes the introducer sheath and a dilator with a first configuration in which the dilator is received in the introducer sheath, and a second configuration in which the dilator is out of contact with the introducer sheath.

In still another aspect, a work-in-progress introducer sheath includes a peel away tube that covers a distal segment of the composite tube, the crosslinked polymer sleeve and the flush transition between the outer surfaces of the composite tube and crosslinked sleeve.

DETAILED DESCRIPTION

Figure 1:
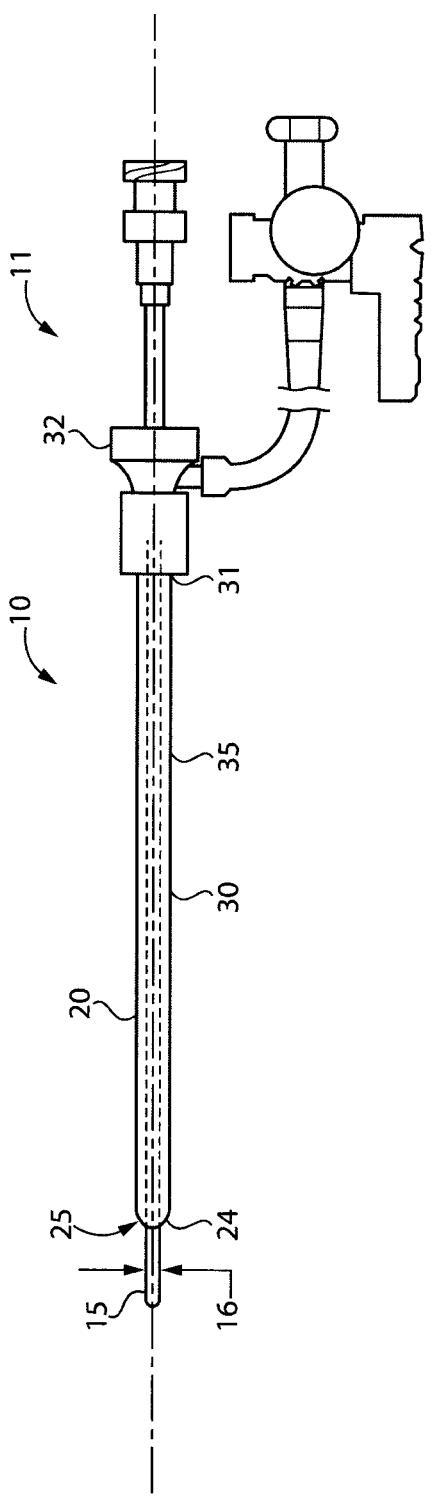
FIG. 1 is an elevational view of medical introducer according to the present disclosure.

Referring initially to FIG. 1, an introducer 10 includes a sheath 20 and a dilator 15 that can have a first configuration 11, as shown, in which the dilator 15 is received in the sheath 20, and a second configuration in which the dilator 15 is out of contact with the sheath 20. Those skilled in the art will recognize that the second configuration can occur during manufacture or after the introducer 10 has been properly positioned in a patient's anatomy. The sheath 20 includes a composite tube 30 extending between a valve 32 and a tip 25. The composite tube 30 includes a braid 33 with a hollow cylindrical shape sandwiched between, and in contact with, an inner polymer tube 34 and an outer thermoplastic tube 35. In one example, the inner polymer tube 34 might be a thermoset plastic, such as PTFE. As used in this disclosure, and as is typical in the art, a thermoset plastic is different from a thermoplastic. The latter being plastically deformable with heat and pressure, whereas the former is not plastically deformable in the presence of the same heat and pressure. The braid 33 may be steel and have a structure well known in the art, but in the context of the present disclosure, a braid is not a coil, which may have less dimensional stability in the present context. In one example, the outer thermoplastic tube may comprise a polyether block amide such as nylon. The composite tube found in COOK® Flexor® Introducer sets is compatible with the teachings of the present disclosure, and need not be taught again here.

Figures 6, 7:
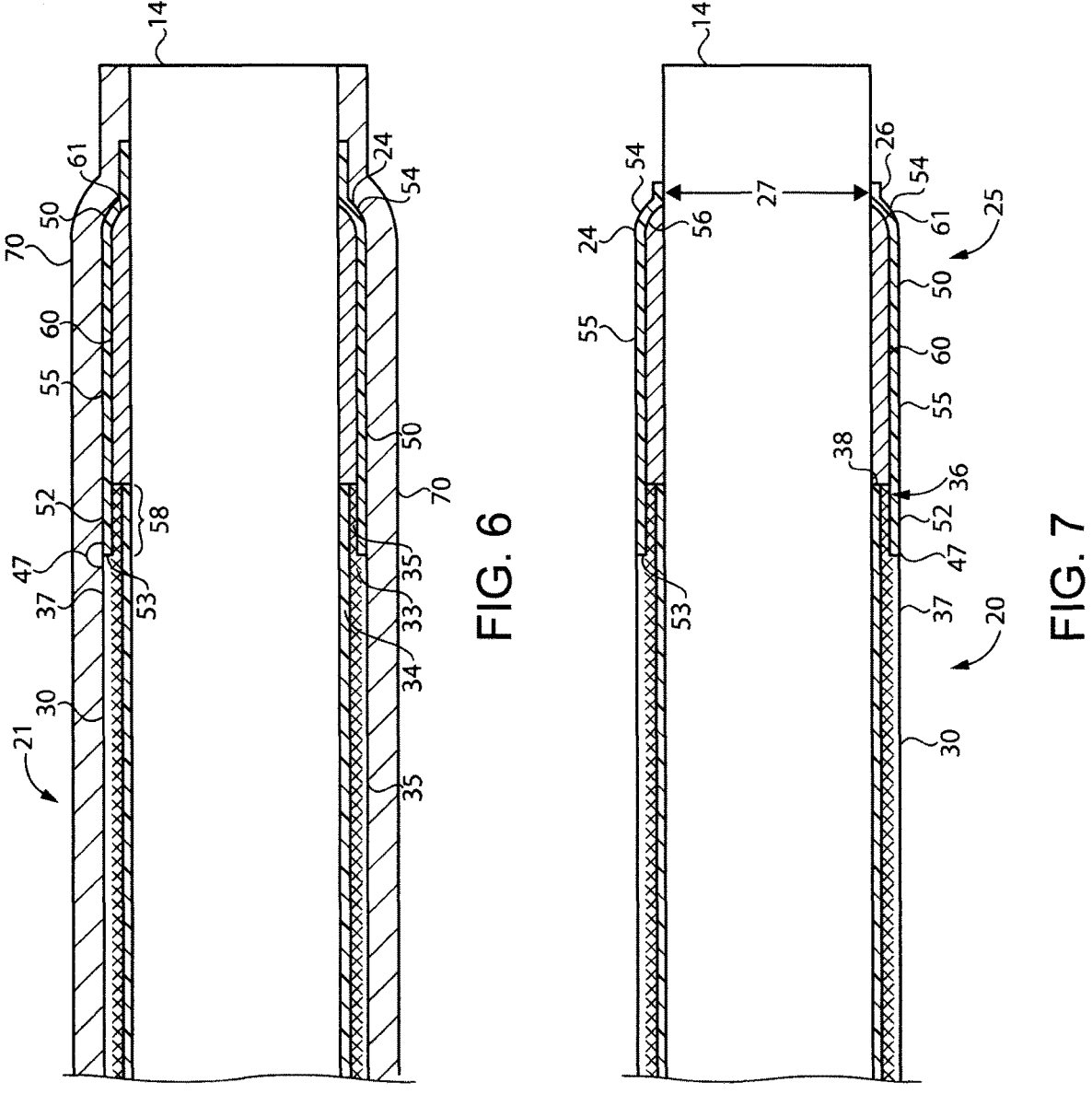
FIG. 6 is a schematic view showing the work-in-progress introducer sheath after heating to a required time and temperature reshapes the outer thermoplastic tube, the crosslinked polymer sleeve and the loaded plastic radiopaque marker.
FIG. 7 is a schematic view showing the introducer sheath after the heat shrink tube has been torn away from the work-in-progress introducer sheath, and any excess crosslinked polymer tube is trimmed away and before being mated with a dilator.
Figures 10, 11:
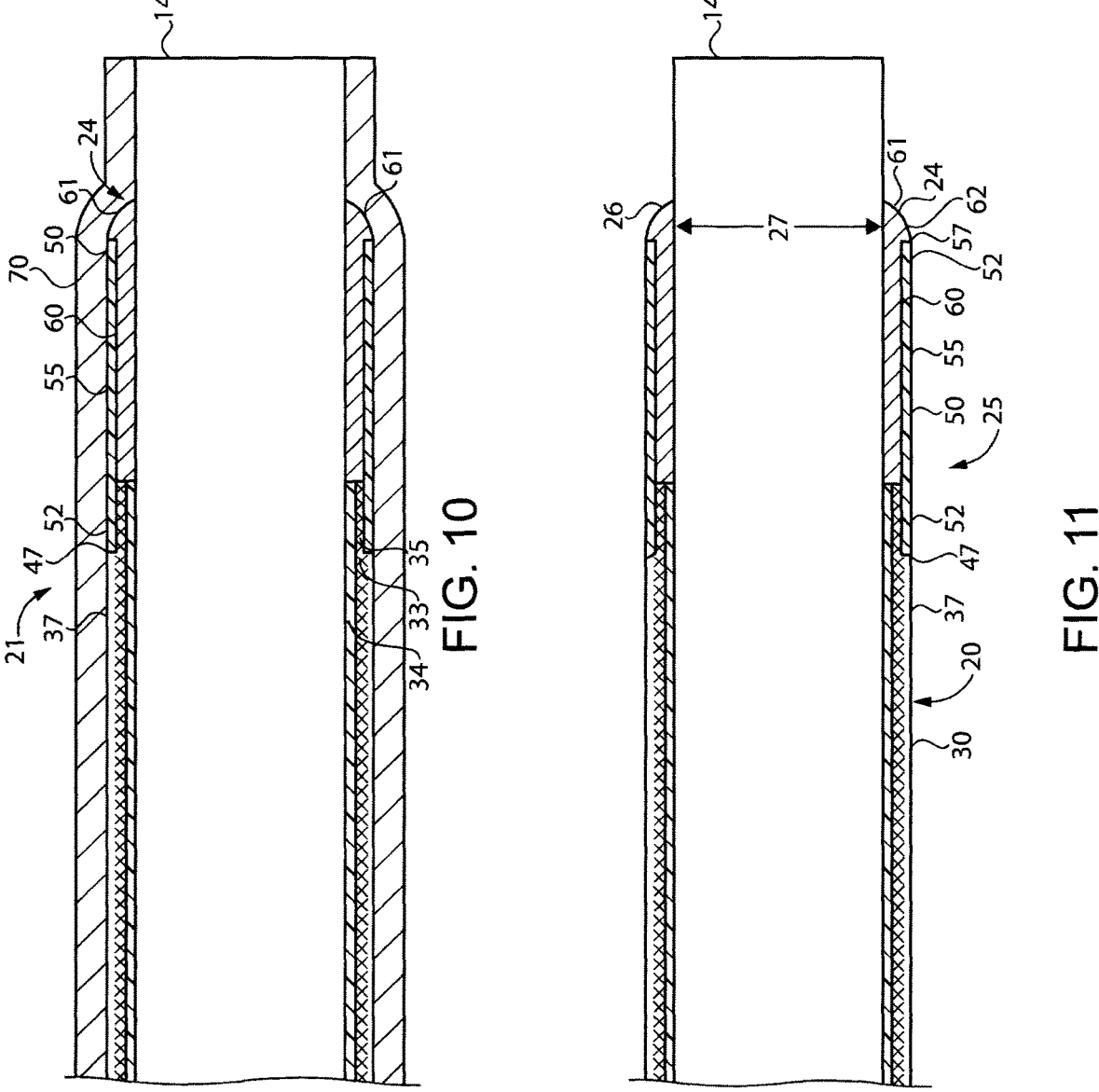
FIG. 10 is a schematic view showing the work-in-progress introducer sheath after heating to a required time and temperature reshapes the outer thermoplastic tube, the crosslinked polymer sleeve and the loaded plastic radiopaque marker.
FIG. 11 is a schematic view showing the introducer sheath after the heat shrink tube has been torn away from the work-in-progress introducer sheath and before being mated with a dilator.

Referring now in addition to the two embodiments shown in FIGS. 7 and 11, respectively, which share feature numbering for similar features. In both embodiments, the tip 25 of the sheath 20 includes a radiopaque marker 60 and a crosslinked polymer sleeve 50, both of which are not parts of the composite tube 30. The radiopaque marker 60 is a loaded thermoplastic, such as a soft tungsten loaded (e.g., 65-80% wt. Tu) polyether block amide material formed initially in a hollow cylindrical shape with a length of maybe three millimeters, for example. The crosslinked polymer sleeve 50 preferably has a pre-shrunk inner diameter sized to slide over a distal segment of the composite tube 30 and the radiopaque marker 60, and a wall thickness preferably less than a wall thickness of the composite tube 30. In one example, crosslinked polymer sleeve 50 might be a polyether block amide heat shrink tube of the type manufactured by Cobalt Polymers. An outer surface 52 at a proximal end 53 of the crosslinked polymer sleeve 50 has a flush transition 47 to an outer surface 37 of the composite tube 30, and a distal portion 55 of the crosslinked polymer sleeve 50 extends distally beyond a distal end 38 of the inner polymer tube 34. The radiopaque marker 60 is shaped to include a tapered segment 61 distal to the flush transition 47. In the embodiment of FIG. 7, the tapered segment 61 of the radiopaque marker 60 is in mold contact with an inner surface 56 of a tapered segment 54 of the crosslinked polymer sleeve 50. In the FIG. 7 embodiment, a distal end segment 26 of the tip 25 includes exactly one layer, which is a portion of the crosslinked polymer sleeve 50. In the FIG. 11 embodiment the tapered segment 24 of tip 25 includes the tapered segment 61 of radiopaque marker 60, which comprises the only layer of the distal end segment 26 of the tip 25. Also in the FIG. 11 embodiment, the crosslinked polymer sleeve 50 may retain a regular cylindrical shape without a taper and stop short of the distal end segment 26. It is also worth noting that in the FIG. 11 embodiment, an outer surface 62 of the radiopaque marker 60 may have a flush transition 57 to the outer surface 52 of the crosslinked polymer sleeve 50. In both embodiments, the radiopaque marker 60 abuts both a distal end 38 of the inner polymer tube 34 and a distal end 39 of the braid 33 so that radiopaque marker is positioned distally of both.

Figures 2, 3:
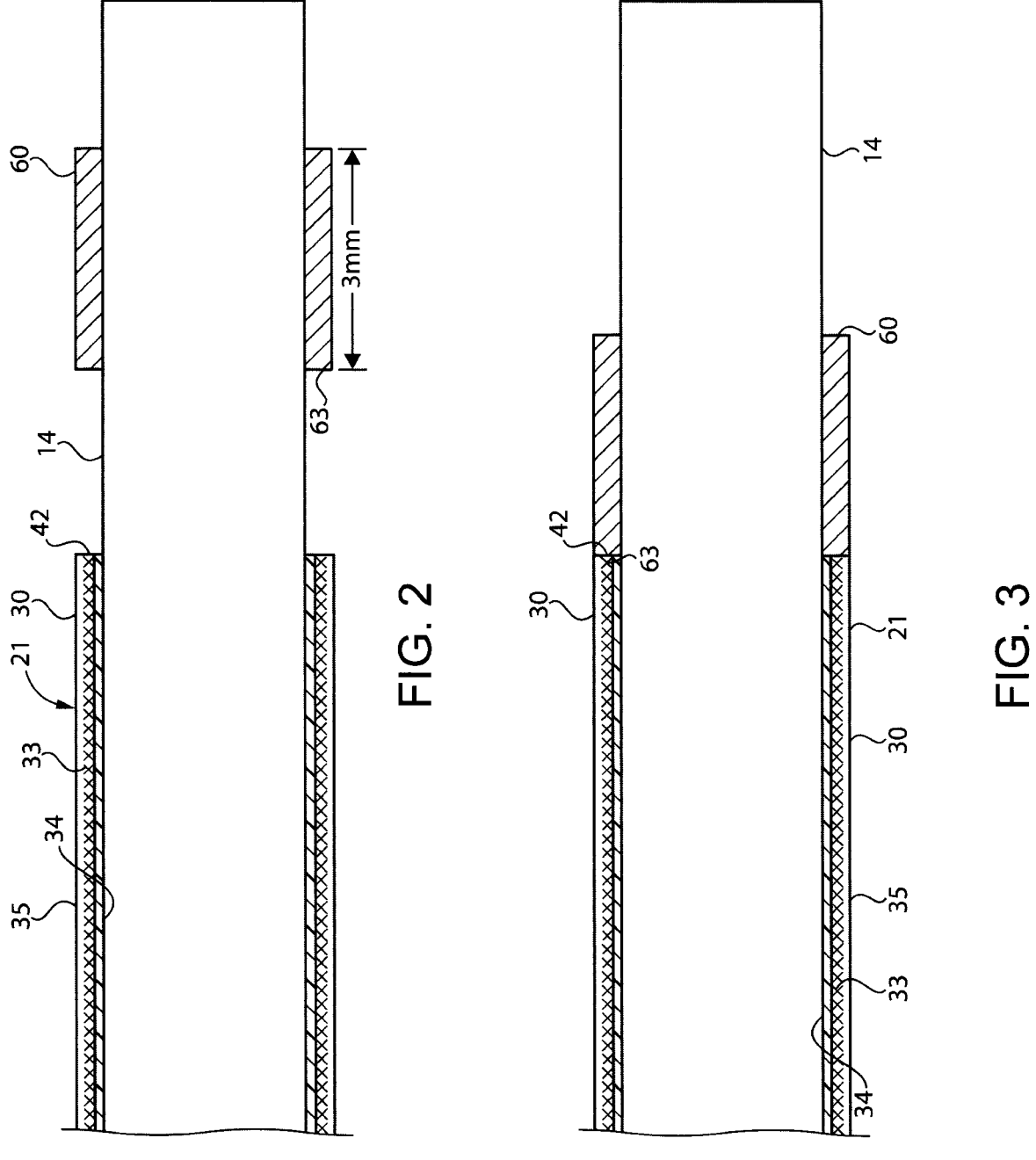
FIG. 2 is a schematic view of a distal end of a work-in-progress introducer sheath supported by a mandrel.
FIG. 3 is a schematic view showing a loaded polymer radiopaque marker abutting a distal end of a composite tube for the work-in-progress introducer sheath.
Figures 4, 5:
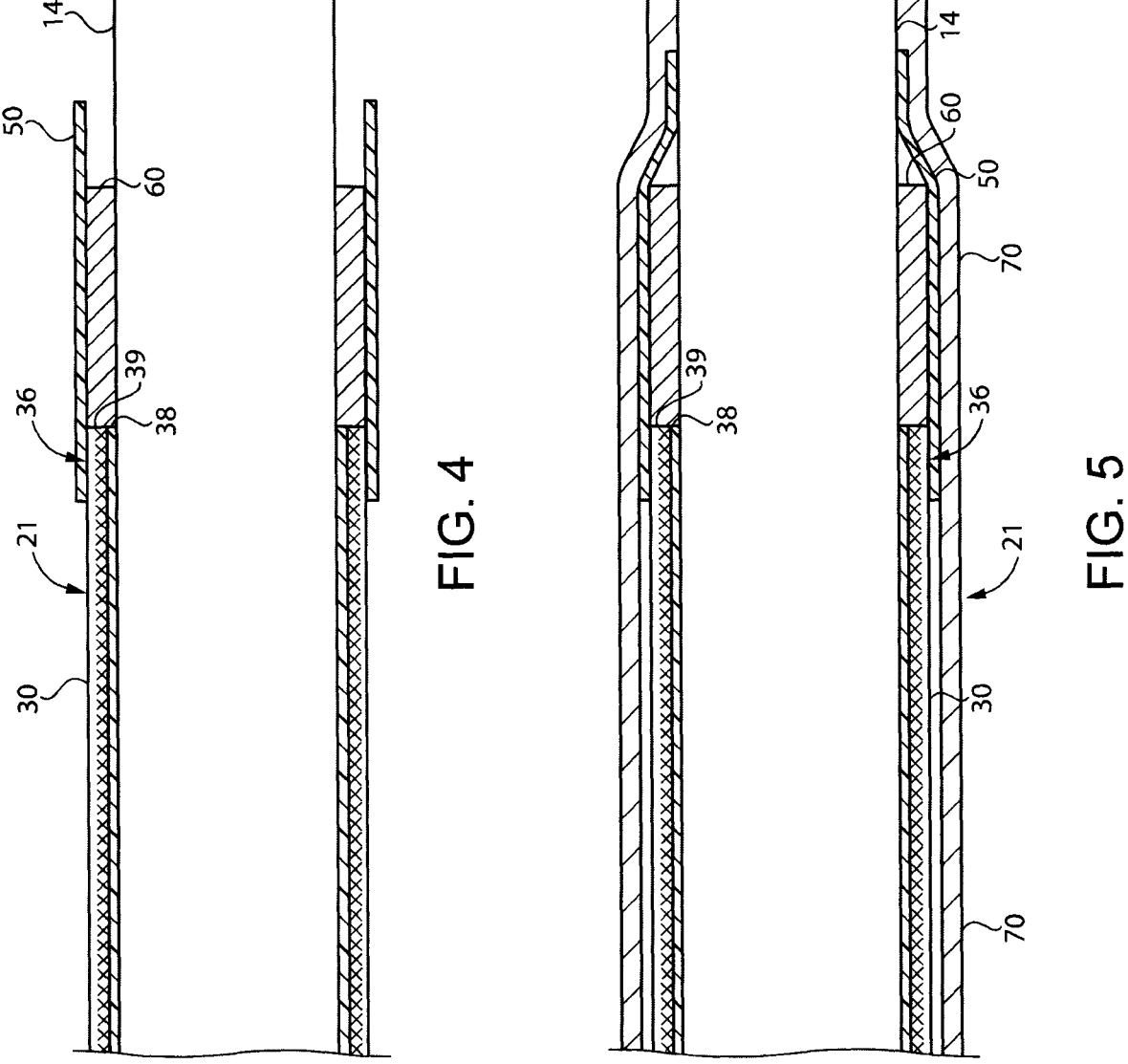
FIG. 4 a crosslinked polymer sleeve slid over the radiopaque marker and a distal end segment of the composite tube.
FIG. 5 is a schematic view showing a heat shrink tube shrunk down to cover the crosslinked polymer sleeve and a distal segment of the composite tube.

Referring now to FIGS. 2-7, example steps for transforming a work-in-progress introducer sheath 21 into an introducer sheath 20 inform the thermal properties and geometry of various components discussed above. For example, FIG. 2 shows a work-in-progress introducer sheath 21 supported on a mandrel 14 that has an outer diameter that corresponds to the outer diameter 16 of the dilator 15 (FIG. 1). A loaded polymer radiopaque marker 60, which may be about 3 mm in length, is being slid on mandrel 14 toward an exposed distal end 42 of composite tube 30. In FIG. 3, A proximal end 63 of the radiopaque marker 60 abuts distal end 42 supported on mandrel 14. FIG. 4 shows after the crosslinked polymer sleeve 50 has been positioned to receive a distal segment 36 of composite tube 30 and an entirety of the radiopaque marker 60. Before the application of any heat, this geometry suggests that both the radiopaque marker 60 and composite tube 30 inner diameters are matched to be freely slidable on mandrel 14, which may have a uniform diameter corresponding to a 5 or 6 French, for example. The outer diameters of composite tube 30 and radiopaque marker 60 are free sliding matches with the preshrunk crosslinked polymer tube 50, which is longer than the radiopaque marker 60. A distal portion of the crosslinked polymer sleeve 50 extends unsupported beyond a distal end 64 of the radiopaque marker 60. FIG. 5 shows the work-in-progress sheath 21 after a peel away tube 70, such as a fluorinated ethylene propylene heat shrink tube, has been heat shrunk down over the entire tip 25. At this point, the heat applied may be insufficient to cause outer thermoplastic tube 35 or loaded polymer radiopaque marker 60 to run or plastically deform. This deformation is responsive to heat and the molding forces produced by the radial shrinkage of crosslinked polymer sleeve 50 and shrinkage of peel away tube 70. Next, as shown in FIG. 6, the assembly may be placed in a bonder and heated to a required temperature and duration that causes both the outer thermoplastic tube 35 and loaded polymer radiopaque marker 60 to flow so that the shrinkage forces of crosslinked polymer sleeve 50 and peel away tube 70 produce a flush transition 47 from an outer surface 52 of sleeve 50 to an outer surface 37 of composite tube 30, and squeeze sleeve 50 and radiopaque marker 60 to produce tapered segment 61 in mold contact with inner surface 56 of tapered segment 54. Preferably, crosslinked polymer sleeve 50 has a higher melting temperature than both outer thermoplastic tube 35 and loaded polymer radiopaque marker 60. Work-in-progress introducer sheath 21 includes a segment 58 with five layers that include portions of the inner polymer tube 34, the braid 33, the outer thermoplastic tube 35, the crosslinked polymer sleeve 50 and the peel away tube 70. FIG. 7 shows the completed tip 25 of the introducer sheath 20 after removal of peel away tube 70 and the trimming away of excess crosslinked polymer sleeve 50, if any.

Preferably, after cooling and removal of mandrel 14, the crosslinked polymer sleeve 50 has some residual elastic hoop stress, especially at its distal end segment 26, so that it has a rest diameter 17 that is smaller than the outer diameter 16 of the dilator 15 where the tip 25 contacts the dilator in the first configuration 11 to provide a tight interface therebetween. By choosing a material for crosslinked polymer sleeve 50 that is visually opaque, any portions of the distal braid that might emerge through the outer thermoplastic tube 35 are covered.

Figures 8, 9:
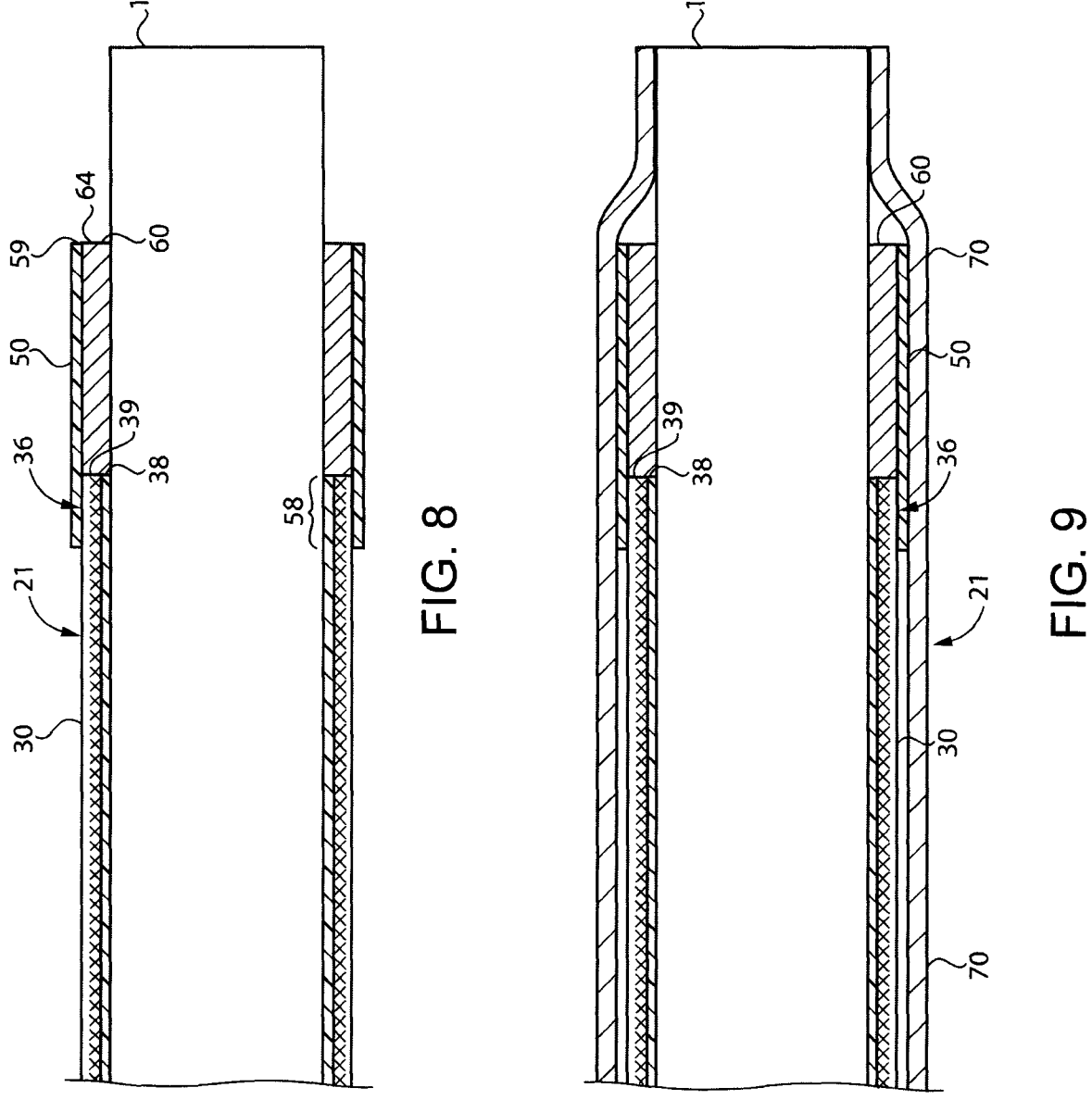
FIG. 8 is a schematic view showing an alternative next step from FIG. 3, with the distal ends of the crosslinked sleeve and radiopaque marker coincide.
FIG. 9 is a schematic view showing a heat shrink tube shrunk down to cover the crosslinked polymer sleeve and a distal segment of the composite tube.

Referring now to FIGS. 2, 3 and 8-11, A slightly different embodiment is created by starting with the distal end 59 of the crosslinked polymer sleeve 50 coinciding with the distal end 64 of the radiopaque marker 60 as shown in FIG. 8, as opposed to the overhanging geometry of FIG. 3. FIG. 9 is similar to FIG. 4 showing after the peel away tube 70 has been heat shrunk down onto the assembly. FIG. 10 shows after the assembly might be placed in a bonding machine at a required time and temperature to flow the outer thermoplastic tube 35 and the radiopaque marker 60 responsive to radial shrinkage of both the crosslinked polymer sleeve 50 and the peel away tube 70. In the first instance, peel way tube 70 applies a molding force to produce a flush transition 47 between the outer surface 52 of crosslinked polymer sleeve 50 and the outer surface 37 of the outer thermoplastic tube 35. The peel away tube 70 is also engineered to produce molding forces to squish some of the radiopaque marker material out to shape a tapered segment 61 and a flush transition 57 between the outer surface 62 of the radiopaque marker and the outer surface 52 of the crosslinked polymer sleeve 50. The transformation from work-in-progress introducer sheath 21 to introducer sheath 20 includes cooling and then removal of the peel away tube 70 as per FIG. 11. Thereafter, mandrel 14 is removed and sheath 20 is mated with an appropriate dilator 15.

INDUSTRIAL APPLICABILITY

The present disclosure finds general application to medical introducers, especially when there is a likelihood of the introducer having to pass through tight and/or scared tissues. By positioning the radiopaque marker at the distal tip of the sheath, a clinician may better visualize with fluoroscopy precisely where the distal opening of the sheath is in the patient's anatomy. The tighter interface between the sheath 20 and the dilator 15 provided by the crosslinked polymer sleeve 50 along with the exterior surface transitions and taper down to the inner supporting dilator helps to ensure smooth insertion through skin, as well as atraumatic and smooth tracking through peripheral arteries. The flush outer surface transitions also reduce the likelihood of tissue snags when the introducer sheath is withdrawn. Usage of the crosslinked polymer sleeve 50 helps to prevent braid 33 exposure during bonding of the tip 25 while reinforcing tip bond strength. The crosslinked polymer sleeve 50 may also act as a protective layer to protect the tungsten loading against UV induced oxidation and embrittlement, and may even impart additional protection when the tip 25 contacts calcified tissue. Finally, the close and preferably elastic fit to the support dilator should significantly reduce insertion forces.

Those skilled in the art will recognize that many variations from the example embodiments described above could be made with departing from the scope of the claims set forth below.

What is claimed is:

1. An introducer comprising:

a sheath and a dilator having a first configuration in which the dilator is received in the sheath, and a second configuration in which the dilator is out of contact with the sheath;

the sheath including a composite tube extending between a valve and a tip, and the composite tube includes a braid with a hollow cylindrical shape sandwiched between, and in contact with, an inner polymer tube and an outer thermoplastic tube;

the tip including a radiopaque marker, which is a loaded thermoplastic, and a crosslinked polymer sleeve that receives a distal segment of the composite tube and at least partially receives the radiopaque marker, and the crosslinked polymer sleeve being longer than the radiopaque marker along an axis of the composite tube;

an outer surface of the crosslinked polymer sleeve has a flush transition to an outer surface of the composite tube at a proximal end of the crosslinked polymer sleeve, and a distal portion of the crosslinked polymer sleeve extends distally beyond a distal end of the inner polymer tube; and the radiopaque marker having a tapered segment distal to the flush transition.

2. The introducer of claim 1 wherein the radiopaque marker abuts a distal end of the braid.

3. The introducer of claim 1 wherein the radiopaque marker abuts the distal end of the inner polymer tube.

4. The introducer of claim 1 wherein the tapered segment of the radiopaque marker is in contact with a tapered segment of the crosslinked polymer sleeve.

5. The introducer of claim 1 wherein the tip has a rest inner diameter that is smaller than an outer diameter of the dilator where the tip contacts the dilator in the first configuration.

6. The introducer of claim 1 wherein the crosslinked polymer sleeve is opaque.

7. The introducer of claim 1 wherein a distal end segment of the tip includes exactly one layer, which is a portion of the crosslinked polymer sleeve.

8. The introducer of claim 1 wherein the radiopaque marker is positioned distally of a distal end of the inner polymer tube;

the radiopaque marker has a tapered segment in contact with the tapered segment of the crosslinked polymer sleeve; and the radiopaque marker is a tungsten loaded material.

9. An introducer sheath comprising:

a composite tube extending between a valve and a tip, and the composite tube includes a braid with a hollow cylindrical shape sandwiched between, and in contact with, an inner polymer tube and an outer thermoplastic tube;

the tip including a radiopaque marker, which is a loaded thermoplastic, and a crosslinked polymer sleeve that receives a distal segment of the composite tube and at least partially receives the radiopaque marker, and the crosslinked polymer sleeve being longer than the radiopaque marker along an axis of the composite tube;

an outer surface of the crosslinked polymer sleeve has a flush transition to an outer surface of the composite tube at a proximal end of the crosslinked polymer sleeve, and a distal portion of the crosslinked polymer sleeve extends distally beyond a distal end of the inner polymer tube; and the radiopaque marker having a tapered segment distal to the flush transition.

10. The introducer sheath of claim 9 wherein the radiopaque marker is entirely positioned distally of a distal end of the inner polymer tube.

11. The introducer sheath of claim 10 wherein the radiopaque marker abuts a distal end of the inner polymer tube.

12. The introducer sheath of claim 11 wherein the radiopaque marker is a tungsten loaded material.

13. The introducer sheath of claim 9 wherein the tapered segment of the radiopaque marker is in mold contact with an inner surface of a tapered segment of the crosslinked polymer sleeve.

14. The introducer sheath of claim 13 wherein a distal end segment of the tip includes exactly one layer, which is a portion of the crosslinked polymer sleeve.

15. The introducer sheath of claim 14 wherein the crosslinked polymer sleeve is opaque.

16. The introducer sheath of claim 9 wherein the tip has a rest inner diameter that is smaller than an outer diameter of a dilator where the tip contacts the dilator in a first configuration.

17. The introducer sheath of claim 16 wherein the radiopaque marker is positioned distally of a distal end of the inner polymer tube.

18. The introducer sheath of claim 17 wherein the tapered segment of the radiopaque marker is in mold contact with an inner surface of a tapered segment of the crosslinked polymer sleeve.

19. A work-in-progress introducer sheath comprising:

a composite tube extending between a proximal end and a tip, and the composite tube includes a braid with a hollow cylindrical shape sandwiched between, and in contact with, an inner polymer tube and an outer thermoplastic tube;

the tip including a radiopaque marker, which is a loaded thermoplastic, and a crosslinked polymer sleeve that receives a distal segment of the composite tube and at least partially receives the radiopaque marker, and the crosslinked polymer sleeve being longer than the radiopaque marker along an axis of the composite tube;

an outer surface of the crosslinked polymer sleeve has a flush transition to an outer surface of the composite tube at a proximal end, and the radiopaque marker having a tapered segment distal to the flush transition;

a peel away tube covering, and in contact with, a distal segment of the composite tube, the flush transition, and the crosslinked polymer sleeve; and a distal portion of the crosslinked polymer sleeve extends distally beyond a distal end of the inner polymer tube.

20. The work-in-progress introducer sheath of claim 19 wherein the tip includes a segment with five layers that includes a portion of the inner polymer tube, a portion of the braid, a portion of the thermoplastic tube, a portion of the crosslinked polymer sleeve and a portion of the peel away tube.

* * * * *